United States Patent
Zi et al.

(10) Patent No.: US 10,687,932 B2
(45) Date of Patent: Jun. 23, 2020

(54) THROMBUS FILTER AND UTILIZATION METHOD THEREOF

(71) Applicant: Venus Medtech (Hangzhou) Inc., Hangzhou, Zhejiang (CN)

(72) Inventors: Zhenjun Zi, Hangzhou (CN); Rongjun Lei, Hangzhou (CN); Shouliang Lv, Hangzhou (CN); Zhifei Zhang, Hangzhou (CN); Jinhu Yu, Hangzhou (CN)

(73) Assignee: Venus Medtech (Hangzhou) Inc, Hangzhou (CN)

( * ) Notice: Subject to any disclaimer, the term of this patent is extended or adjusted under 35 U.S.C. 154(b) by 232 days.

(21) Appl. No.: 14/646,091

(22) PCT Filed: Oct. 14, 2013

(86) PCT No.: PCT/CN2013/085167
§ 371 (c)(1),
(2) Date: Jul. 17, 2015

(87) PCT Pub. No.: WO2014/079291
PCT Pub. Date: May 30, 2014

(65) Prior Publication Data
US 2015/0366650 A1    Dec. 24, 2015

(30) Foreign Application Priority Data

Nov. 23, 2012 (CN) .......................... 2012 1 0484480

(51) Int. Cl.
*A61F 2/01* (2006.01)
*A61B 17/221* (2006.01)

(52) U.S. Cl.
CPC ............ *A61F 2/013* (2013.01); *A61B 17/221* (2013.01); *A61F 2/01* (2013.01);
(Continued)

(58) Field of Classification Search
CPC . A61B 2017/2215; A61B 17/22; A61B 17/50; A61B 17/221; A61B 17/22031;
(Continued)

(56) References Cited

U.S. PATENT DOCUMENTS

| 4,611,594 A * | 9/1986 | Grayhack ............ A61B 17/221 606/127 |
| 2005/0261705 A1* | 11/2005 | Gist ...................... A61B 17/221 606/113 |

(Continued)

FOREIGN PATENT DOCUMENTS

| CN | 1328808 | 1/2002 |
| CN | 201086640 | 7/2008 |
| CN | 10297332 | 3/2013 |
| JP | 3660931 | 4/2005 |

*Primary Examiner* — Katherine H Schwiker
(74) *Attorney, Agent, or Firm* — Raymond Sun

(57) ABSTRACT

A thrombus filter has a sheath, a thrombus intercepting net having an intercepting port, and an overfill prevention umbrella being a meshed structure that always surrounds the entire thrombus intercepting net. The overfill prevention umbrella has an umbrella stand and an umbrella surface, and is self-biased such that, at body temperature, the umbrella surface is configured to always converge towards the center of the intercepting port. The thrombus filter assumes a first position when the thrombus intercepting net is released from the sheath, where the distal opening of the overfill prevention umbrella is pushed open by the intercepting port. The thrombus filter assumes a second position when the thrombus intercepting net is retrieved into the sheath, where the umbrella surface converges towards the center of the intercepting port, and the open end of the umbrella surface is constricted to prevent the thrombus from escaping.

7 Claims, 5 Drawing Sheets

(52) U.S. Cl.
CPC . *A61B 2017/2215* (2013.01); *A61F 2002/011* (2013.01); *A61F 2002/016* (2013.01); *A61F 2210/0014* (2013.01); *F04C 2270/0421* (2013.01)

(58) Field of Classification Search
CPC ........ A61B 17/3207; A61B 2017/2212; A61B 2017/2217; A61B 2017/22034; A61B 2017/22035; A61B 2017/00867; A61B 2017/320716; A61B 2017/320708; A61B 2017/320725; A61B 2017/32075; A61B 2017/320758; A61B 2017/320783; A61B 2017/320733; A61B 2017/320741; A61B 2017/320766; A61B 2017/320775; A61B 2017/320791; A61B 17/22032; A61B 2017/22037; A61F 2002/011; A61F 2210/0014; A61F 2/01; A61F 2/013; A61F 2002/016; A61F 2002/018; A61F 2002/015; A61M 1/34; A61M 25/0074; A61M 2025/0079; A61M 2025/109
USPC .................................................. 606/48, 200
See application file for complete search history.

(56) References Cited

U.S. PATENT DOCUMENTS

| | | | |
|---|---|---|---|
| 2005/0283166 A1* | 12/2005 | Greenhalgh | A61B 17/221 606/113 |
| 2006/0195118 A1* | 8/2006 | Richardson | A61B 17/221 606/113 |
| 2008/0103522 A1 | 5/2008 | Steingisser | |
| 2009/0192485 A1* | 7/2009 | Heuser | A61B 17/221 604/500 |
| 2009/0222035 A1* | 9/2009 | Schneiderman | A61B 17/221 606/200 |
| 2010/0268264 A1* | 10/2010 | Bonnette | A61B 17/221 606/200 |
| 2011/0190806 A1 | 8/2011 | Wittens | |
| 2012/0041449 A1* | 2/2012 | Eckhouse | A61B 17/221 606/127 |
| 2012/0059356 A1 | 3/2012 | Di Palma | |
| 2013/0018387 A1* | 1/2013 | Diamant | A61B 17/221 606/127 |
| 2014/0074144 A1* | 3/2014 | Shrivastava | A61B 17/22031 606/200 |

* cited by examiner

THROMBUS FILTER AND UTILIZATION METHOD THEREOF

TECHNICAL FIELD

The present invention relates to a blood vessel filter and utilization method thereof, in particular to a thrombus filter and utilization method thereof.

BACKGROUND

With the wide application of interventional operation in the world, the complications resulted therefrom are also increasingly occurred. For example, in the interventional aortic valve replacement operation, due to the severe stenosis and calcification in aorta, there is a need to support and replace the original aortic valve via the aortic valve, but most of the severely stenosed and calcified aortas will bring about a reduced inner diameter of the blood flow channel, at this time, in general, the original calcified valve is first pre-expanded with a balloon, during this process, part of the calcified clots will be removed during the expansion process, or the thrombus generated during the operation will enter coronary artery, brain and lower limb vessels, etc., with the blood flow, thus leading to vascular embolism, and finally resulting in the patient's death or paralysis.

In order to solve the above problems, the Chinese Patent Publication No. CN1515326A, published on Jul. 28, 2004, entitled "thrombus filter", discloses a thrombus filter, comprising a thrombus intercepting net, a guide wire, a distal connecting piece and a proximal connecting piece, wherein the thrombus intercepting net is in a funnel-shaped meshed structure made from nickel titanium shape memory alloy wire, with a coating film with filtration pores, the retracting line of the nickel titanium memory alloy wire is wound through the mesh pores of the opening portion of the thrombus intercepting net, then connected to the proximal connecting piece, the rear portion of the meshed structure of the thrombus intercepting net is connected to the distal connecting piece, and the front end of the distal connecting piece is provided with a guiding head. The opening portion of the thrombus interceptor is connected to the nickel titanium memory alloy wire to make the thrombus interceptor tightly fitted to the inner wall of the blood vessel under the restoring force of the nickel titanium memory alloy wire, so as to effectively filter the thrombus; when the thrombus interceptor is retracted, the retracting line first tightens the opening of the funnel-shaped thrombus intercepting net, and can effectively prevent the thrombus from escaping, therefore the thrombus interceptor can improve the recovery rate of thrombus, reduce the risks of embolism in coronary artery, brain and lower limb blood vessels, etc., and has the advantages of simple structure, convenient operation, good filtering, high safety and reliability, and can be widely used in a variety of angioplasty and thrombolysis as a overfill prevention umbrella for the thrombus or the removed clot, so as to reduce the operation risk and improve the success ratio of operation The above thrombus filter only discloses the case that the opening portion of the intercepting net faces toward the proximal end (control end), and does not describe the thrombus intercepting means where the opening portion of the intercepting net faces toward the distal end (away from the control end), and such technology has not been effectively solved. At the same time, in the stenosed blood vessel channel, how the thrombosis filter not only can capture the thrombus or the removed clot, but also does not cause interference to the implantation process, is a problem to be solved.

SUMMARY

In order to overcome the defects in the prior art, the present invention provides a thrombus filter which not only can effectively prevent the thrombus from escaping when it is retracted after capturing thrombus, but also has a simple structure, and convenient operation.

The technical solution of the present invention is a thrombus filter, comprising a sheath, a thrombus intercepting net with an intercepting port, a first pushing piece for driving the thrombus intercepting net in and out of the sheath, and a control handle for controlling the first pushing piece, also provided with an overfill prevention umbrella, wherein the opening of the overfill prevention umbrella faces the same direction as the intercepting port, and the overfill prevention umbrella surrounds the outside the thrombus intercepting net;

a second pushing piece, which is located in the sheath to push and pull the overfill prevention umbrella;

the overfill prevention umbrella comprises an umbrella stand and an umbrella surface, the umbrella stand has one end connected to the second pushing piece, and the other end connected to the umbrella surface, and the open end of the umbrella surface is in a constricted memory shape;

when the thrombus intercepting net is released, the opening of the overfill prevention umbrella is pushed open by the intercepting port of the thrombus intercepting net; and when the thrombus intercepting net is retracted, the umbrella surface of the overfill prevention umbrella covers the intercepting port of thrombus intercepting net, and the open end of the umbrella surface is constricted to prevent the thrombus from escaping.

Preferably, both the thrombus intercepting net and the overfill prevention umbrella are in a meshed structure, and the meshed structure is made from a memory alloy.

Preferably, the thrombus intercepting net is in a meshed structure, the overfill prevention umbrella is consisted of an umbrella stand and a coating film with filtration pores coated on the umbrella stand, and the umbrella stand is made from a memory alloy.

Preferably, the thrombus intercepting net is in a meshed structure, the umbrella surface of the overfill prevention umbrella is in a meshed form, the umbrella stand is a support rod connected to the umbrella surface, and the umbrella surface is made from a memory alloy.

Preferably, thrombus intercepting net is consisted of a framework and a coating film with filtration pores coated on the framework, the umbrella surface of the overfill prevention umbrella is in a meshed form, the umbrella stand is a support rod connected to the umbrella surface, and the umbrella surface is made from a memory alloy.

Preferably, the second pushing piece is in a tubular shape, the second pushing piece is slidingly surrounding the first pushing piece, and is coaxially located with the first pushing piece.

Preferably, the first pushing piece is in a tubular shape, and the hollow portion inside the tubular first pushing piece forms a transport channel.

Preferably, the umbrella surface is in an annular shape, the outer edge of the annular shape is connected to the umbrella stand.

Preferably, one end of the thrombus intercepting net is an intercepting port, the other end of the thrombus intercepting net is a net bottom, the net bottom part is extended into the sheath and connected to the first pushing piece.

The present invention has the beneficial effects as follows: the overall structure is simple, the operation is convenient, when the thrombus intercepting net and the overfill prevention umbrella are released, the thrombus generated during the operation process can be effectively retrieved, and when the overfill prevention net is retracted after capturing thrombus, the escape of thrombus can be effectively prevented.

The present invention provides a method for utilizing the thrombus filter according to claim 1, comprising the steps of:

(1) a sheath loaded with a thrombus intercepting net and an overfill preventionumbrella is transported to a position in blood vessel required to capture thrombus;

(2) the sheath is retracted to expose the intercepting net and the overfill prevention umbrella outside the sheath and release them together, the intercepting port of the thrombus intercepting net is opened, at the same time the opening of the overfill prevention umbrella is pushed open, and the thrombus is captured via the reverse direction of the blood flow by the thrombus intercepting net;

(3) upon the capture of thrombus is finished, the thrombus intercepting net is retracted via the first pushing piece, the umbrella surface of the overfill prevention umbrella is moved forward with respect to the thrombus intercepting net, and covers the intercepting port, and the open end of the umbrella surface is constricted under the constriction force of memory shape so as to prevent the thrombus from escaping;

(4) when the opening of the overfill prevention umbrella is completely constricted, the sheath is pushed forward to retract the overfill prevention umbrella back into the sheath;

(5) the sheath loaded with the thrombus intercepting net and the overfill prevention umbrella is withdrawn from the blood vessel.

As compared with the prior art, the present invention has the beneficial effects as follows, the thrombus filter has a simple utilization method and operation procedure, is convenient to use, and not only has a good filtering effect on the thrombus generated during the operation process, but also can effectively prevent the thrombus from escaping when it is extracted after capturing thrombus.

DESCRIPTION OF EMBODIMENTS

Figure 1:
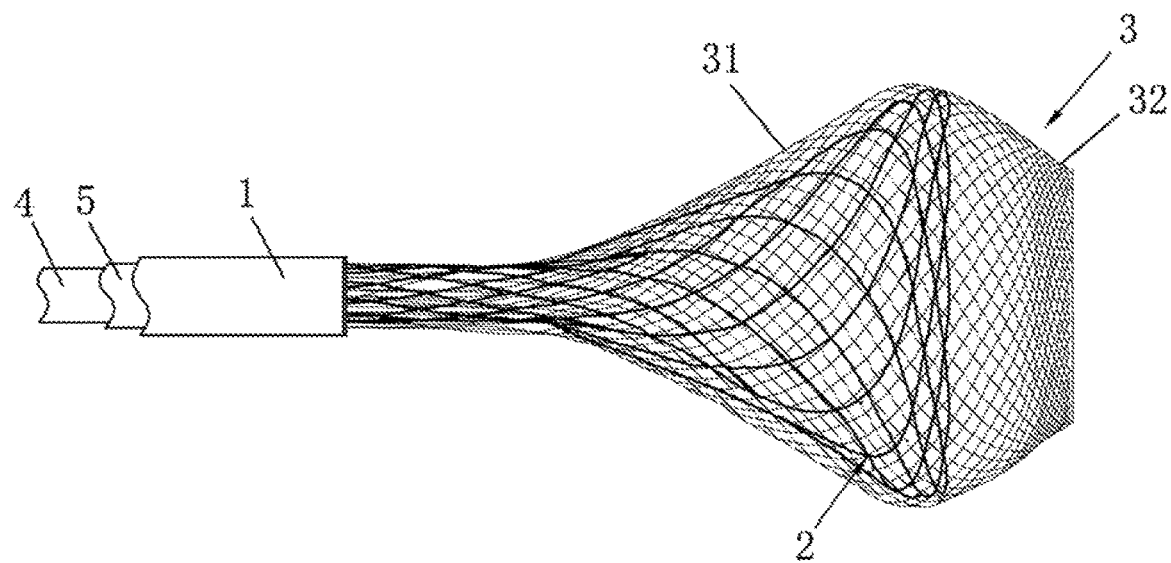
FIG. 1 is a structural schematic diagram of example 1 of the present invention.

The technical solutions of the present invention will be further illustrated below in combination with drawings of the description and the particular examples. It should be understood that the particular examples described herein are only used to explain the present invention, but not intended to make any limitation.

As shown in FIG. 1-10, the thrombus filter of the present invention comprises a sheath 1 and a control handle (not shown), in the initial state, a thrombus intercepting net 2 and a overfill prevention umbrella 3, and a first pushing piece 4 and a second pushing piece 5 connected to the thrombus intercepting net 2 and the overfill prevention umbrella 3, respectively, and controlled by the control handle are accommodated in the sheath 1. Among them, the first pushing piece 4 and the second pushing piece 5 are in a tubular shape, the second pushing piece 5 has a bigger diameter and coaxially surrounds the outside the first pushing piece 4; the thrombus intercepting net 2 is in a funnel shape, wherein one end of the thrombus intercepting net 2 is an intercepting port, the other end of the same is a net bottom, the net bottom part is connected to the first pushing piece 4 which is located inside the sheath 1; the net bottom part also has a vent corresponding to the pipe orifice of the first pushing piece 4, the vent can be used as a channel for a balloon, interventional device, etc., when they are in the same path with the thrombus filter. Therefore, when there is a need for importing the balloon and interventional device, etc., into the blood vessel, it is unnecessary to make an additional opening on the blood vessel 1, thus minimizing the harm to human body. Of course, the first pushing piece 4 and the second pushing piece 5 can also employ a fitting between a cylindrical shape and a tubular shape, or other structures which can realize the pushing function, all of these embodiments fall in the scope of protection of the present invention.

The overfill prevention umbrella 3 surrounds the peripheral wall of the converged thrombus intercepting net 2, and the overfill prevention umbrella 3 can be divided into two parts, the umbrella stand 31 and the umbrella surface 32, the umbrella stand 31 surrounds the peripheral wall of the thrombus intercepting net 2. In the present invention, the first pushing piece 4, the second pushing piece 5, the umbrella stand 31 and the umbrella surface 32, have their ends adjacent to the control handle, as the proximal ends, and the ends away from the control handle, as the distal ends, the proximal end of the umbrella stand 31 is connected to the distal end of the second pushing piece 5; the proximal end of the umbrella surface 32 is connected to the distal end of the umbrella stand 31, the open end of the umbrella surface 32 faces the same direction as the intercepting port of the thrombus intercepting net 2, the opening on the open end of umbrella surface 32 is in an actively constricted state, which is used to cover the intercepting port of the thrombus intercepting net 2.

Memory alloy material is a new material which has the advantages of being nonmagnetic, and providing wear resistance, corrosion resistance, non-toxicity, etc., when it is cooled, in the austenite phase state, it is soft and can be easily compressed into the bridge pipe, and when it is released in body, it turns into a martensite phase, and restores its design shape.

In order to facilitate the implementation of the process, the umbrella stand 31 and the umbrella surface 32 can be in a one-piece structure, both of them are made from a memory alloy material, and the production for the one-piece structure is simple. In addition, the umbrella stand 31 and the umbrella surface 32 can also be in a composite structure, both of them are connected together by means of a suture or connecting piece, so as to further reduce the consumptive materials and the overall size.

The materials for the umbrella stand 31 and the umbrella surface 32 can be different, the umbrella stand 31 can be made from a material which is contracted toward the axial direction of the sheath in the original state, and is flexible; the umbrella stand 31 is moved with the expansion and convergence of the thrombus intercepting net 2, particularly, after the thrombus intercepting net 2 is opened, the umbrella stand 31 will also be pushed open.

The control handle can make a pull and push operation on the first pushing piece 4, at the same time the control handle can be an intrinsic part on the proximal end of the first pushing piece 4, and can also be separately constructed with the first pushing piece 4 and assembled and arranged. The control handle not only can control the pushing motion of the thrombus intercepting net 2, but also can control the pushing motion of the sheath 1 and the overfill prevention umbrella 3, when the displacement of the overfill prevention umbrella 3 is controlled and supported via the second pushing piece 5 and the sheath 1 is retracted, the movement of the overfill prevention umbrella 3 is limited by the second pushing piece 5, and the backward friction force is overcome, based on the same reasoning, the first pushing piece 4 is linked with the thrombus intercepting net 2 to provide the forward and backward movements in the sheath 1. After the sheath 1 loaded with the thrombus intercepting net 2 and the overfill prevention umbrella 3 is transported to the designated position in the blood vessel I, the sheath 1 is retracted, the overfill prevention umbrella 3 and thrombus intercepting net 2 are maintained in their relative positions by the relatively fixed second pushing piece 5 and first pushing piece 4, and placed in the blood vessel.

According to the characteristics of the thrombus intercepting net 2 and the overfill prevention umbrella 3, the present invention comprises at least the following four examples, but not limited thereto.

Example 1

As shown in FIG. 1, both the thrombus intercepting net 2 (bold black line) and the overfill prevention umbrella 3 are in a meshed structure, the meshed structure is woven from a memory alloy, wherein the thrombus intercepting net 2 is in a open state at the body temperature, and the overfill prevention umbrella 3 is in a constricted state at the body temperature, and the expansion force produced in the thrombus intercepting net 2 under the expansion tendency is higher than the constriction force in the overfill prevention umbrella 3 under the constricted state, that is, if the thrombus intercepting net 2 is opened at the body temperature, the overfill prevention umbrella 3 will be subjected to a force and pushed open by the thrombus intercepting net 2. The open end of the umbrella surface 32 of the overfill prevention umbrella 3 is in a constricted memory shape, the open end of the umbrella surface 32 can be always maintained to converge toward the center, that is, the coverage on the intercepting port of the thrombus intercepting net 2 is achieved. The position distal from the intercepting port on the thrombus intercepting net 2 is connected to the first pushing piece 4, and the thrombus intercepting net 2 can be freely pushed in the sheath 1 via the first pushing piece 4; the umbrella stand 31 of the overfill prevention umbrella 3 is connected to the second pushing piece 5, and the overfill prevention umbrella 3 can be freely pushed in the sheath 1 via the second pushing piece 5.

Example 2

Figure 2:
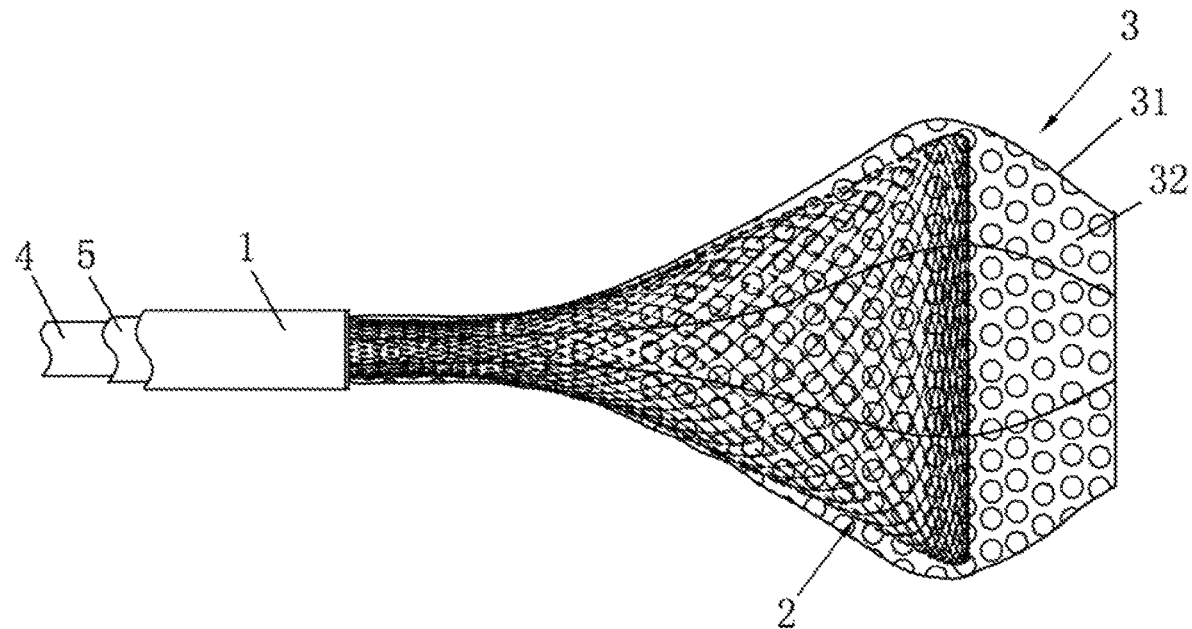
FIG. 2 is a structural schematic diagram of example 2 of the present invention.

As shown in FIG. 2, the thrombus intercepting net 2 is in a meshed structure, the meshed structure is woven from a memory alloy, the thrombus intercepting net 2 is in a open state at the body temperature. The umbrella surface 32 of the overfill prevention umbrella 3 is a coating film having filtration pores, the umbrella stand 31 (bold black line) is made from a memory alloy strip, the umbrella stand 31 is axially arranged around the sheath 1, and the longitudinal direction of the umbrella stand 31 is identical to the direction of the sheath 1, the memory shape for the distal end of the umbrella stand 31 is an arc bending toward the axial center, the proximal end of the umbrella stand 31 is connected to the second pushing piece 5, at the body temperature, the distal end of the umbrella stand 31 is converged toward the axial direction of the sheath 1, wherein the umbrella surface 32 is coated on the peripheral wall of the umbrella stand 31, and moved with the expansion and convergence of the umbrella stand 31.

Example 3

Figure 3:
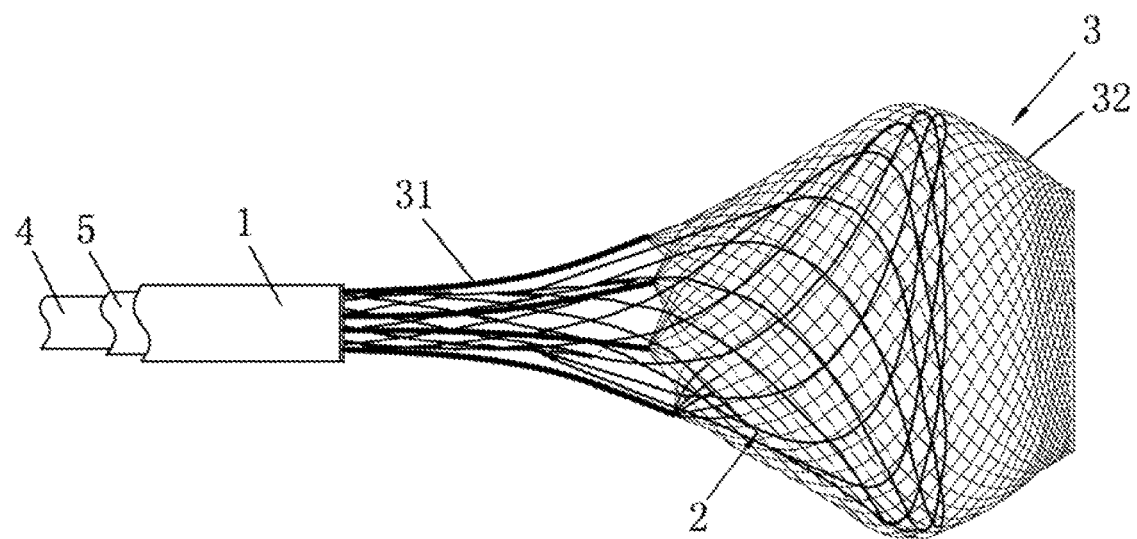
FIG. 3 is a structural schematic diagram of example 3 of the present invention.

As shown in FIG. 3, the thrombus intercepting net 2 (bold black line) is in a meshed structure, the meshed structure is woven by a memory alloy, and the thrombus intercepting net 2 is in an open state under the body temperature. The umbrella surface 32 of the overfill prevention umbrella 3 is in a meshed structure that is woven from a memory alloy wire, wherein the memory state of the opening of the umbrella surface 32 is a converged state; the umbrella stand 31 (bold black line, which is more bold than that of the thrombus intercepting net 2) is a support rod connected to umbrella surface 32, the two ends of the support rod are connected to the second pushing piece 5 and the umbrella surface 32 respectively.

The thrombus intercepting nets 2 in examples 1, 2 and 3 are woven from a metal wire having a support force, it is pushed open by a balloon and shaped; and can also be made from memory alloy materials, and at the body temperature, it is actively expanded by restoring to the expanded memory shape.

Example 4

Figure 4:
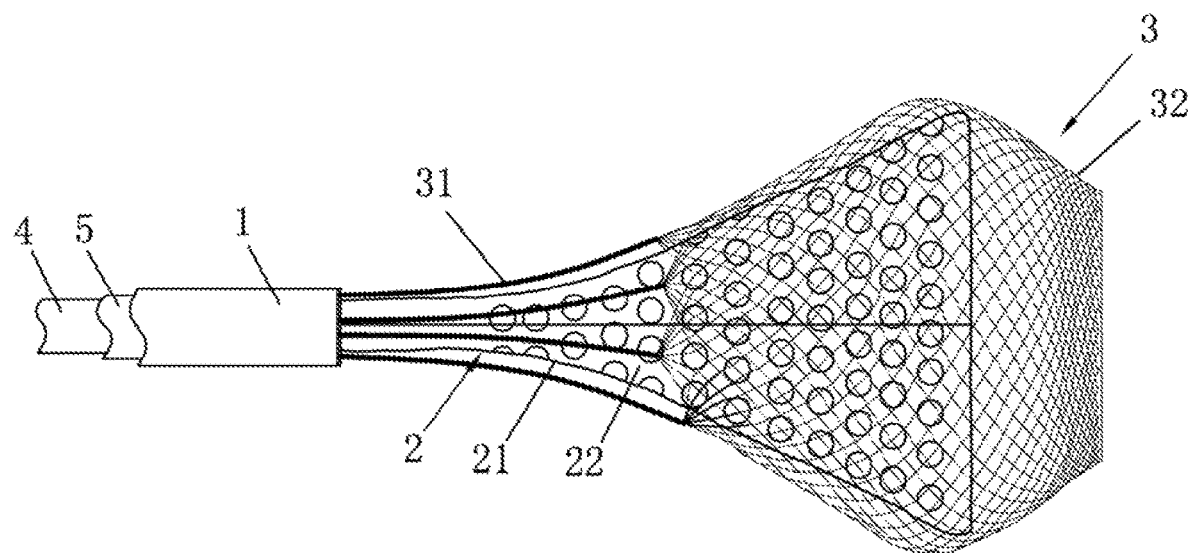
FIG. 4 is a structural schematic diagram of example 4 of the present invention.

As shown in FIG. 4, the thrombus intercepting net 2 is consisted of a framework 21 (bold black line) and a coating film 22 with filtration pores, wherein the coating film 22 is coated on the peripheral wall of the framework 21, the framework 21 is made from a memory alloy strip, one end of the framework 21 is connected to the first pushing piece 4, and at the body temperature, the part extending away from the first pushing piece 4 on the framework 21 will be opened towards the direction away from the axis of the sheath 1, wherein the coating film 22 is coated on the peripheral wall of the framework 21, and moved with the expansion and convergence of the framework 21. The umbrella surface 32 of the overfill prevention umbrella 3 is in a meshed structure that is woven by a memory alloy wire, wherein the memory state of the umbrella surface 32 is a converged state; the umbrella stand 31 (bold black line, which is more bold than that of framework 21) is a support rod connected to umbrella surface 32, the two ends of the support rod are connected to the second pushing piece 5 and the umbrella surface 32, respectively.

The framework of the thrombus intercepting net 2 in example 4 is a metal rod with a support force, it is pushed open by a balloon and shaped; and can also be made from a memory alloy material, and at the body temperature, it is actively expanded by restoring to the expanded memory shape.

Example 5

As shown in FIGS. 5-8, the thrombus intercepting net 2 is consisted of a framework 21 and a coating film 22 with filtering holes, wherein the coating film 22 is coated on the peripheral wall of the framework 21, the framework 21 is made from a memory alloy strip, one end of the framework 21 is connected to the first pushing piece 4, at the body temperature, the part extending away from the first pushing piece 4 on the framework 21 will be opened towards the direction away from the axis of the sheath 1, wherein the coating film 22 is coated on the peripheral wall of the framework 21, and moved with the expansion and convergence of the framework 21. The open end of the umbrella surface 32 of the overfill prevention umbrella 3 is in a constricted memory shape, and the open end of the umbrella surface 32 can be always maintained to converge toward the center, that is, the coverage on the intercepting port of the thrombus intercepting net 2 can be achieved.

The coating films in the above examples are thin films of polymeric material, the thin films of polymeric material generally refer to the thin films of medical polymeric material, such as medical polytetrafluoroethylene film, medical polyurethane film, medical silicon gel film, etc. In addition, the thrombus intercepting net 2 and the overfill prevention umbrella 3 can also have other claimed structures other than the abovementioned structure combinations, without limiting to the 5 cases in the examples.

In the present invention, although there are various examples, the operation procedure and principle in each of the examples are the same, and the utilization method of the thrombus filter is described in detail in example 5 below.

Figure 5:
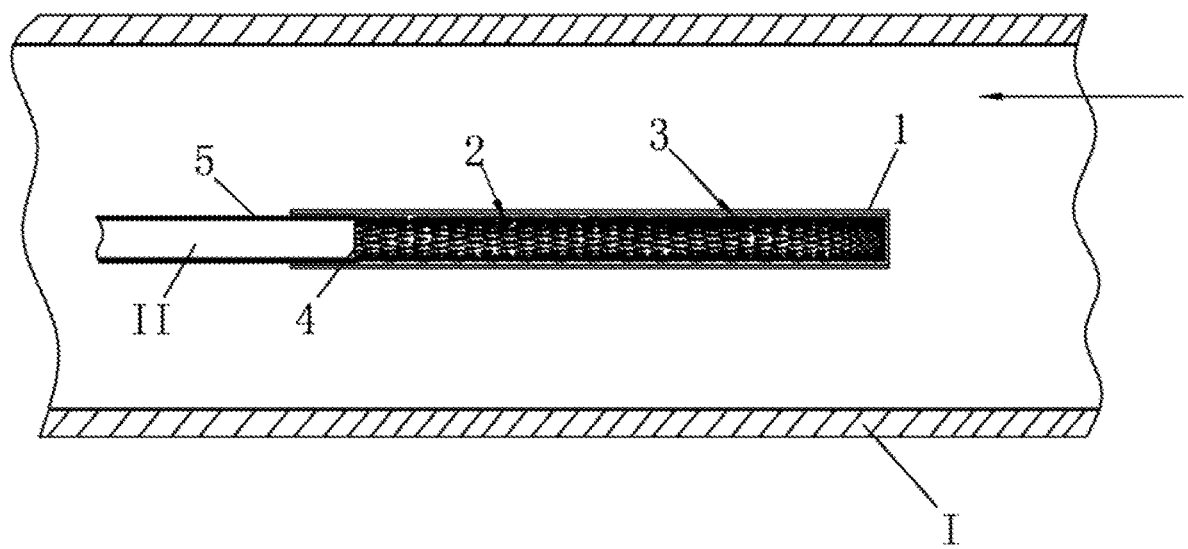
FIG. 5 is a structural schematic diagram of example 5 of the present invention, when the thrombus filter is placed into the blood vessel.

Step 1: As shown in FIG. 5 (in this Figure, the thrombus intercepting net 2 and the overfill prevention umbrella 3 are in an overlapped state and located in the sheath 1), the thrombus filter is placed into the blood vessel I. The sheath 1 loaded with the thrombus intercepting net 2 and the overfill prevention umbrella 3 is transported into the designated position in the blood vessel I. The arrow direction shows the flow direction of the blood mixed with the thrombus 6.

Figure 6:
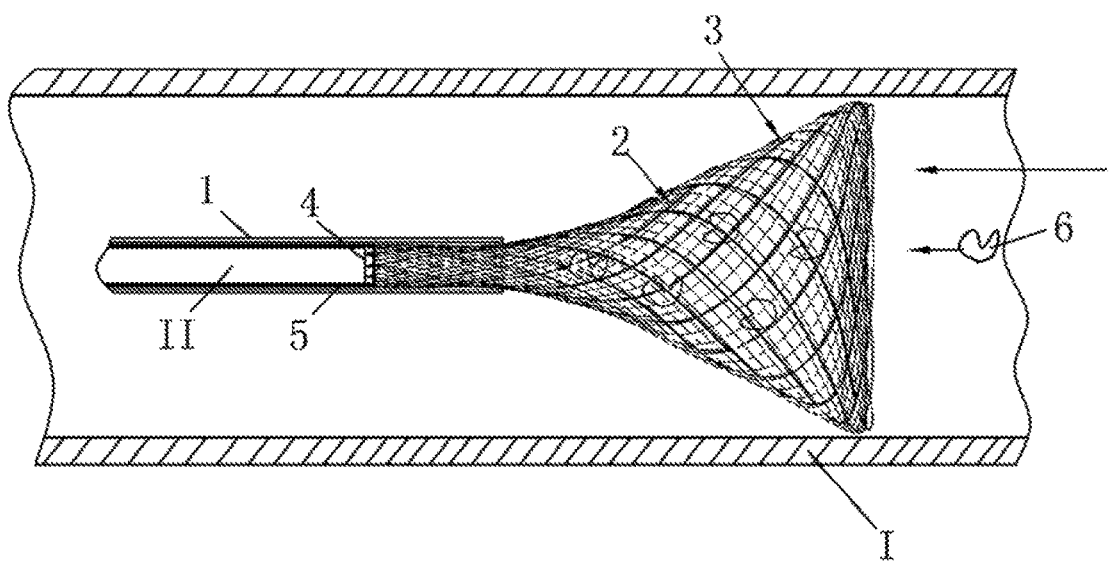
FIG. 6 is a structural schematic diagram of example 5 of the present invention, when the thrombus is captured by the thrombus filter.

Step 2: As shown in FIG. 6 (the thrombus intercepting net 2 and the overfill prevention umbrella 3 are in an overlapped state, and parts of them are exposed outside the sheath 1, at this time, the thrombus intercepting net 2 and the overfill prevention umbrella 3 are the same part in the figure, without significant difference), the thrombus 6 is captured by the thrombus filter. When the sheath 1 loaded with the thrombus intercepting net 2 and the overfill prevention umbrella 3 is moved to the designated position in the blood vessel I, then the sheath 1 is pulled backwards, at the same time, the overfill prevention umbrella 3 and the thrombus intercepting net 2 are pushed via the first pushing piece 4 and the second pushing piece 5, to make the overfill prevention umbrella 3 and the thrombus intercepting net 2 overcame the backward force (such force mainly refers to friction force) and maintain their position, that is, the overfill prevention umbrella 3 and the thrombus intercepting net 2 are maintained to hold a relative still with respect to the blood vessel I by the pushing of the first pushing piece 4 and the second pushing piece 5.

At this point, if the thrombus intercepting net 2 is made from a memory alloy material, and the original state of the thrombus intercepting net 2 is in an open state, the thrombus intercepting net 2 is actively deployed in the blood vessel; if the thrombus intercepting net 2 is made from a stainless steel metal, at first, the thrombus intercepting net 2 is expanded to a suitable size by a balloon; at the same time the overfill prevention umbrella 3 which surrounds the peripheral wall of the thrombus intercepting net 2 is also pushed open.

As required, after the thrombus intercepting net 2 and the overfill prevention umbrella 3 are released, the steps of transportation, placement, and retraction of the surgical instruments are carried out via the channel II in the core of the second pushing piece 5, all of the processes are carried out under a protected state.

Figure 7:
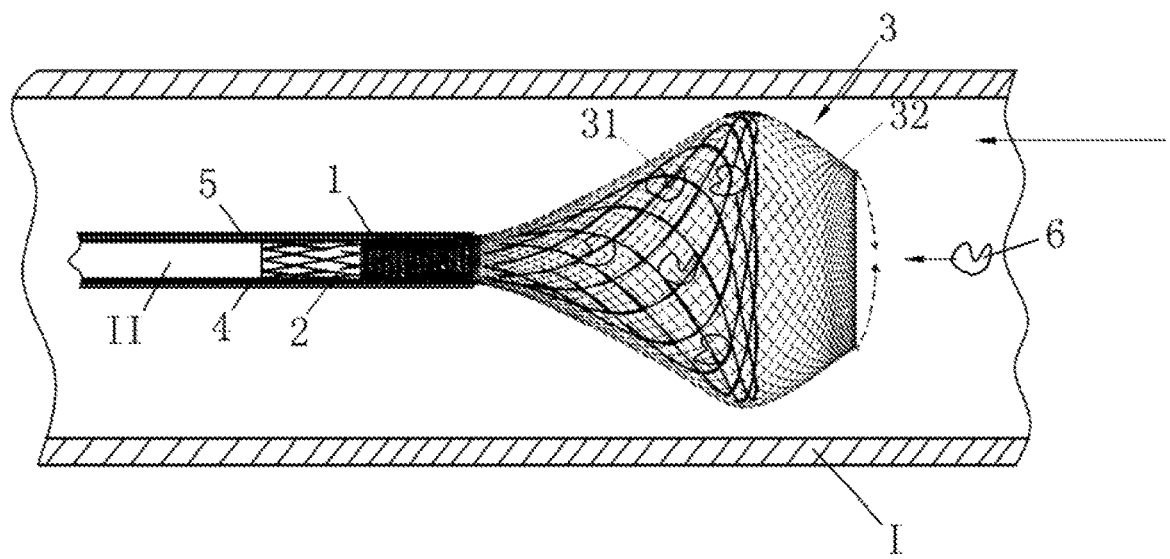
FIG. 7 is a structural schematic diagram of example 5 of the present invention, when the intercepting net of the thrombus filter is retracted.

Step 3: As shown in FIG. 7, the intercepting net of the thrombus filter is retracted. After the device implantation process is finished, and when the conjugated capture work of thrombus 6 is finished, the thrombus intercepting net 2 is pulled to return back into the sheath 1 via the first pushing piece 4, during this process, the thrombus intercepting net 2 and the overfill prevention umbrella 3 are staggered with respect to each other at the intercepting port of the thrombus intercepting net 2, that is, the thrombus intercepting net 2 is moved backward and retracted into the overfill prevention umbrella 3, and the overfill prevention umbrella 3 is maintained to hold still with respect to the blood vessel I, so as to avoid injury to the blood vessel I when the thrombus intercepting net 2 is retracted, and the overfill prevention umbrella 3 is moved forward with respect to the thrombus intercepting net 2, and the umbrella surface 32 covers above the intercepting port of the thrombus intercepting net 2 under the constricted memory shape. According to the staggered distance, there will appear to be a gradual or even complete separation of the overlapped parts between the umbrella surface 32 of the overfill prevention umbrella 3 and the thrombus intercepting net 2, at this time the umbrella surface 32 will gradually or even completely cover above the intercepting port of the thrombus intercepting net 2. That is, the umbrella surface 32 of the overfill prevention umbrella 3 will exceed the intercepting port of the thrombus intercepting net 2 and converge toward the center of the intercepting port, so as to achieve the coverage on the intercepting port, which is equivalent to that the diameter of the intercepting port is reduced under the effect of umbrella surface 32, so that a lid-like structure is formed and covers the intercepting port, thereby preventing the thrombus 6 from escaping from the intercepting port. When the open end of the opening of the overfill prevention umbrella 3 is completely closed due to its constricted memory shape (it is possible for the opening to not be completely closed, but since the converged opening is very small, so the thrombus 6 will not escape through the opening, and it is therefore understood that the opening is considered to be completely closed), the thrombus 6 obtained by filtrating from the blood vessel I is encapsulated in the thrombus intercepting net 2 by the overfill prevention umbrella 3. In FIG. 7, the thrombus intercepting net 2 is not completely in place, that is, the overfill prevention net 3 does not completely cover the intercepting port of the thrombus intercepting net 2, at this time, it is necessary for the thrombus intercepting net 2 to be retracted, until the overfill prevention net 3 completely covers the intercepting port of the thrombus intercepting net 2, then the sheath 1 is pushed forward to retract the overfill prevention net 3 and the thrombus intercepting net 2.

In the present invention, there are no explicit definition on the distinguished boundaries between the umbrella surface 32 and umbrella stand 31 on the overfill prevention umbrella 3, as long as in the above situations, the umbrella surface 32 can cover the intercepting port. Among them, when the umbrella surface 32 of the overfill prevention umbrella 3 and the intercepting port of the thrombus intercepting net 2 are staggered with each other, all of the parts hanging outside the intercepting port will collected towards the center of the intercepting port under the constriction force, and the diameter of the intercepting port is reduced, so as to avoid the escape of thrombus 6 from the intercepting port when the thrombus intercepting net 3 and the overfill prevention umbrella 3 are retracted into the sheath 1. The first pushing piece 4 continuously pulls the thrombus intercepting net 2 until the opening of the overfill prevention umbrella 3 is completely constricted, at this time, the overfill prevention umbrella 3 can completely avoid the escape of thrombus 6 from the thrombus intercepting net 2.

Figure 8:
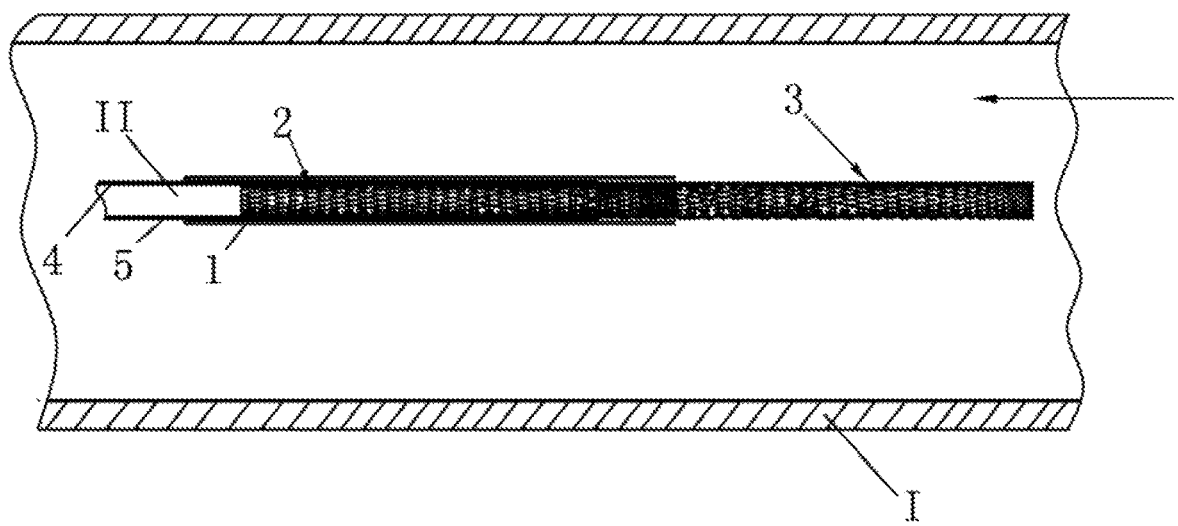
FIG. 8 is a structural schematic diagram in example 5 of the present invention, when the thrombus filter is retracted.
Figure 9:
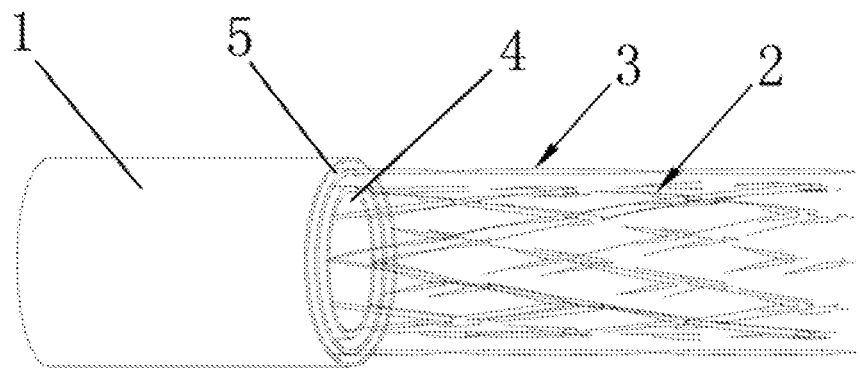
FIG. 9 is a local structural schematic diagram of the example of the present invention.
Figure 10:
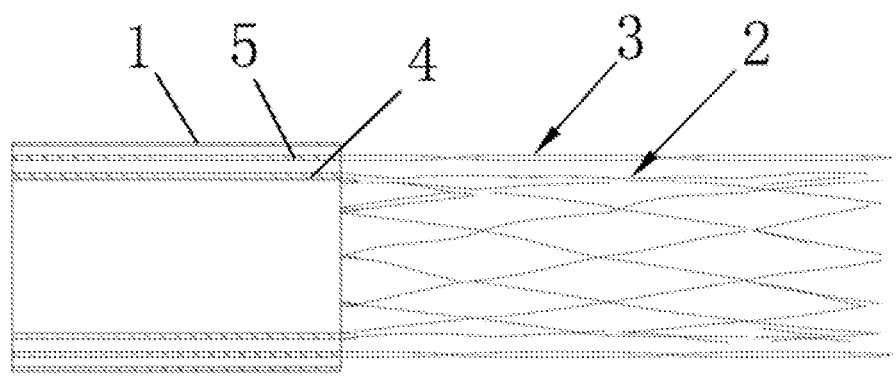
FIG. 10 is a section view of FIG. 9.

Step 4: As shown in FIG. 8, the thrombus filter is retracted. When the opening of the overfill prevention umbrella 3 is completely constricted, the sheath 1 is pushed to make it move forward, the overfill prevention umbrella 3 is completely accommodated into the sheath 1 gradually from the rear of the overfill prevention umbrella 3, so that the thrombus filter can accomplish the filtration of the blood in the blood vessel I, and at the same time can prevent the escape of thrombus 6 when the thrombus intercepting net 2 is retracted, and ensure the stability and safety of the environments in the blood vessel I. As the mucous membrane of the inner wall of the blood vessel I to be protected is frail, when the overfill prevention umbrella 3 is located outside the sheath 1 and inside the blood vessel I, there should not be a relative movement between the overfill prevention umbrella 3 and the blood vessel I, if not, the outer wall of the overfill prevention umbrella 3 will easily scrape the inner wall of the blood vessel I, so as to cause an injury or even lesion on the blood vessel I, therefore, when the thrombus intercepting net 2 and the overfill prevention umbrella 3 are released and retracted, it can be achieved mainly by the relative backward and forward movement of the sheath 1. In addition, in order to further protect the inner wall of the blood vessel I, the bending part of the overfill prevention umbrella 3 and the thrombus intercepting net 2, in a memory state, is in an arc structure.

Step 5: The sheath 1 loaded with the thrombus intercepting net 2 and the overfill prevention umbrella 3 is withdrawn from the blood vessel I.

In the present invention, the umbrella surface 32 has at least the following three states: before the thrombus intercepting net 2 is released, the umbrella surface 32 is located inside the sheath 1 and surrounds the peripheral wall of the thrombus intercepting net 2; when the thrombus intercepting net 2 is released, the umbrella surface 32 is located in the periphery of the thrombus intercepting net 2 and expanded by the support of the thrombus intercepting net 2; and when the thrombus intercepting net 2 is retracted, the umbrella surface 32 is converged from the periphery of the intercepting port of the thrombus intercepting net 2 towards the center of the intercepting port, forming a coverage on the intercepting port. The present invention has the advantages as follows: the overall structure is simple, the operation is convenient, and after the thrombus intercepting net 2 and the overfill prevention umbrella 3 are released, the thrombus 6 generated during the operation process can be effectively retrieved, and when the overfill prevention net 3 is retracted, the escape of thrombus 6 can effectively prevented.

The invention claimed is:

1. A thrombus filter comprising:
   a sheath;
   a thrombus intercepting net having a distal end, a proximal end, and an intercepting port positioned at the distal end, wherein the intercepting port has a center;
   a first pushing piece connected to the thrombus intercepting net;
   an overfill prevention umbrella having a proximal end and a distal end with a distal opening that is adjacent to the intercepting port, wherein the overfill prevention umbrella is a meshed structure;
   a second pushing piece which is located in the sheath and is connected to the overfill prevention umbrella;
   wherein the thrombus intercepting net and the overfill prevention umbrella are retained inside the sheath when the thrombus filter is delivered to a treatment site;
   wherein the overfill prevention umbrella comprises an umbrella stand and an umbrella surface with the umbrella stand having a first end connected to the second pushing piece and a second end connected to the umbrella surface, and wherein the umbrella surface has an open end defining the distal opening, wherein the overfill prevention umbrella is configured such that at body temperature, the umbrella surface converges towards the center of the intercepting port;
   wherein the thrombus filter assumes a first position when the thrombus intercepting net is released from the sheath, where the distal opening of the overfill prevention umbrella is pushed open by the intercepting port of the thrombus intercepting net, wherein in the first position the distal end of the overfill prevention umbrella aligned with the distal end of the thrombus intercepting net and the proximal end of the overfill prevention umbrella aligned with the proximal end of the thrombus intercepting net;
   wherein the thrombus filter assumes a second position when the thrombus intercepting net is retrieved into the sheath, and in the second position the umbrella surface of the overfill prevention umbrella converges towards the center of the intercepting port of the thrombus intercepting net and the open end of the umbrella surface is constricted to prevent the thrombus from escaping, wherein the thrombus intercepting net is movable with respect to the overfill prevention umbrella such that the thrombus intercepting is configured in use to only be retracted relative to the overfill prevention umbrella.

2. The thrombus filter of claim 1, wherein the thrombus intercepting net is in a first meshed structure and the meshed structure of the overfill prevention umbrella is a second meshed structure, and wherein the first and second meshed structures are woven from a memory alloy.

3. The thrombus filter of claim 1, wherein the second pushing piece is tubular and slidably surrounds the first pushing piece such that the second pushing piece is coaxially arranged with the first pushing piece.

4. The thrombus filter of claim 3, wherein the first pushing piece is tubular and has a hollow portion that defines a transport channel.

5. The thrombus filter of claim 1, wherein the umbrella surface has an annular shape and an outer edge that is connected to the umbrella stand.

6. The thrombus filter of claim 1, wherein the distal end of the thrombus intercepting net is the intercepting port, the thrombus intercepting net having a proximal end that is a net bottom, and the net bottom extends into the sheath and is connected to the first pushing piece.

7. A method for utilizing a thrombus filter, comprising the steps of:
   (1) providing a thrombus filter comprising:
   a sheath;
   a thrombus intercepting net having a distal end, a proximal end, and an intercepting port positioned at the distal end, wherein the intercepting port has a center;
   a first pushing piece connected to the thrombus intercepting net;
   an overfill prevention umbrella having a proximal end and a distal end with a distal opening that is adjacent to the intercepting port, wherein the overfill prevention umbrella is a meshed structure;
   a second pushing piece which is located in the sheath and is connected to the overfill prevention umbrella;
   wherein the overfill prevention umbrella comprises an umbrella stand and an umbrella surface with the umbrella stand having a first end connected to the second pushing piece and a second end connected to the umbrella surface, and wherein the umbrella surface has an open end defining the distal opening, wherein the overfill prevention umbrella is configured such that at body temperature, the umbrella surface converges towards the center of the intercepting port;
   (2) loading the sheath with the thrombus intercepting net and the overfill prevention umbrella, and transporting the sheath to a position in a blood vessel for capturing thrombus;
   (3) retracting the sheath to expose the thrombus intercepting net and the overfill prevention umbrella together outside the sheath such that the distal opening of the overfill prevention umbrella is pushed open by the intercepting port of the thrombus intercepting net to a first position, wherein in the first position the distal end of the overfill prevention umbrella aligned with the distal end of the thrombus intercepting net and the proximal end of the overfill prevention umbrella aligned with the proximal end of the thrombus intercepting net;
   (4) capturing thrombus into the thrombus intercepting net by positioning an opening of the thrombus intercepting net in a direction opposite to the direction of blood flow;
   (5) upon completing the capture of thrombus, retracting the thrombus intercepting net to a second position using the first pushing piece so that the umbrella surface of the overfill prevention umbrella is in a forward location with respect to the thrombus intercepting net, wherein in the second position, the umbrella surface of the overfill prevention umbrella covers the intercepting port and converges towards the center of the intercepting port of the thrombus intercepting net to prevent the thrombus from escaping, wherein the only relative movement between the thrombus intercepting net and the overfill prevention umbrella is retraction of the thrombus intercepting net;
   (6) pushing the sheath forward to retract the thrombus filter into the sheath; and
   (7) withdrawing the sheath from the blood vessel.

* * * * *